United States Patent [19]
Kerver

[11] Patent Number: 5,951,594
[45] Date of Patent: Sep. 14, 1999

[54] AIR CORE ANTENNA FOR IMPLANTABLE DEVICE AND METHOD OF PRODUCTION

[75] Inventor: Harry B. A. Kerver, Duiven, Netherlands

[73] Assignee: Vitatron Medical B.V., Dieren, Netherlands

[21] Appl. No.: 09/067,681

[22] Filed: Apr. 28, 1998

[51] Int. Cl.⁶ ............................. A61N 1/375; A61N 1/36
[52] U.S. Cl. ................. 607/32; 607/36; 607/60
[58] Field of Search ............................. 607/5, 9, 32, 36, 607/57, 60

[56] References Cited

U.S. PATENT DOCUMENTS

| | | |
|---|---|---|
| 4,428,378 | 1/1984 | Anderson et al. . |
| 4,441,498 | 4/1984 | Nordling . |
| 5,052,388 | 10/1991 | Sivula et al. . |
| 5,370,669 | 12/1994 | Daglow et al. . |
| 5,782,891 | 7/1998 | Hassler et al. . |

Primary Examiner—William E. Kamm
Assistant Examiner—Carl H. Layno
Attorney, Agent, or Firm—Michael J. Jaro; Harold Patton

[57] ABSTRACT

There is provided an air core antenna, and method of production of same, suitable for use in implantable device, the antenna being used for telemetric communication with an outside programmer unit. The air core antenna is fabricated upon a hybrid substrate, which substrate is subsequently processed to contain electronic circuits for use in the implantable device. A groove is milled into the perimeter side walls of the antenna, and the coil wire is wound within the groove, the two ends of the coil then being attached to connector pads on the substrate. There is thus provided an antenna which is integrally incorporated into the substrate so that space requirements of the antenna are minimized, providing an antenna which has a sufficient loop area to provide the receiving and transmission characteristics required of a modern programmable implanted device. The production process of the air core antenna is suitable for use on an automated assembly line, eliminating separate mounting of an antenna, and minimizing manual interactions.

18 Claims, 4 Drawing Sheets

AIR CORE ANTENNA FOR IMPLANTABLE DEVICE AND METHOD OF PRODUCTION

FIELD OF THE INVENTION

This invention relates to air core antennas for implantable devices and, more particularly, air core antennas for pacemakers, and the method of production of same.

BACKGROUND OF THE INVENTION

Implantable medical devices, such as cardiac pacemakers, have become increasingly sophisticated. It is standard in the art to make such devices programmable, in the sense that the implanted device can receive telemetry signals from an external programmer which program its mode of operation, or operating parameters. Indeed, in modern cardiac systems there is extensive two-way communication between an implanted cardiac pacemaker and an external programmer device. Thus, data collected by the pacemaker and stored can be downloaded to the programmer, and programming instructions and other data can be transmitted from the programmer to the pacemaker. As another example of programming, see application Ser. No. 08/890,435, filed Jul. 9, 1997, and titled "Pacemaker System With Enhanced Programmable Modification Capacity", assigned to the same assignee as this invention, an implanted pacemaker can be designed to receive new software releases, each software release being downloaded into memory within the pacemaker to provide a functional modification of the operating characteristics of the pacemaker.

The technical circuitry required for both the programmer and the implanted device is well known in the art. The programmer generates telemetry signals, usually electromagnetic, which are received by an antenna within the implanted device. The antenna must be small enough to be accommodated efficiently within the housing of the device, but must also possess desired operating characteristics of sensitivity, directivity, etc. Since space within the implanted device is at a premium, it is essential that the antenna design be as efficient as possible. Modern pacemakers generally employ air core antennas for this purpose. The prior art discloses a number of different types of air core antennas. For example, air core coil antennas are wound on a separate coil carrier that is mounted on a circuit substrate. In another arrangement, the air core coil antenna is wound around a frame that is used for mounting the pulse generator assembly, comprising the battery and other circuitry, within the implantable pulse generator can. In another embodiment, ferrite core antennas are utilized, which may be mounted on or at the side of a hybrid circuit portion of the pulse generator.

Antenna designs currently in use for implanted medical devices generally are compromise designs which leave much room for improvement, either in the characteristics of the antenna as fabricated, or in the production process itself. What is needed in the art, particularly for implantable devices such as pacemakers where physical space is at a premium, but integrity of communication is critical, is an antenna design which allows efficient production steps adapted for an automated assembly line, as well as providing an antenna which does not separately take up space, and which is sensitive to linking with the programmer.

SUMMARY OF THE INVENTION

In view of the need in the art as above described, there is provided an air core antenna and method of production of same, particularly adapted for an implanted medical device such as a cardiac pacemaker wherein the air core antenna is wound in a mechanical groove around the outer perimeter of a substrate on which is mounted hybrid electrical circuitry. A substrate, either ceramic or printed circuit board (pcb), is milled to its exact dimensions, and a groove within the thickness of the substrate is milled at the same time. An antenna coil is wound in the groove, and its two ends are attached to connection pads on the substrate. The connection pads are then probed to provide a current pulse through the coil, resulting in a heating of the coil to a degree which makes the windings fuse together, causing a fixation of the windings while maintaining isolation between the windings. The pads can then be further probed to test the coil to see that it has the correct inductance and resistance. After this, the circuitry is placed on the substrate, and the coil is connected to the circuitry.

There is thus provided a substrate which contains multiple wiring layers and circuitry, mostly concentrated toward the center of the substrate, while the coil antenna is tucked within a groove around the substrate. This provides a large area coil which is efficiently positioned to minimize space allocation for the coil, and can be produced as part of an automated process for fabricating the finished hybrid substrate.

DETAILED DESCRIPTION OF THE PREFERRED EMBODIMENTS

Figure 1:
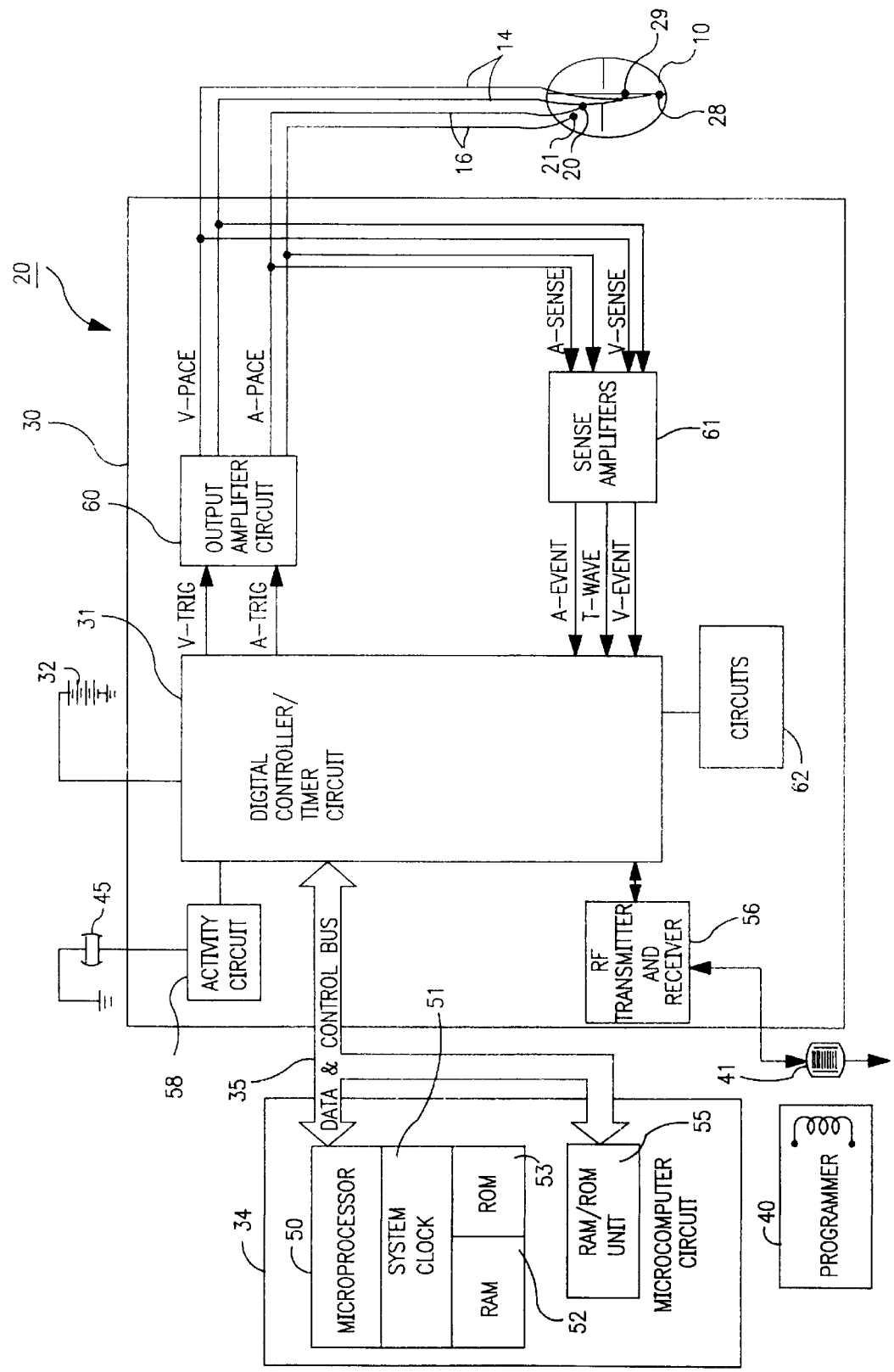
FIG. 1 is a block diagram of a typical implantable cardiac pacemaker system, illustrating how the implantable pacemaker is in communication with an external programmer.

FIG. 1 is a block functional diagram of a pacemaker 20, as connected to a human heart 10. The circuitry illustrated is all located within a conductive housing or can of the pacemaker (not shown), and bipolar leads 14 and 16 are illustrated schematically for connecting the pacemaker to the heart. It is to be understood that while a pacemaker provides a preferred environment of the air core antenna of this invention, the scope of the invention is not limited to pacemaker embodiments.

The pacemaker is divided generally into a microcomputer circuit 34 and a pacing circuit 30. A pulse generator circuit 60 includes a ventricular pulse generator circuit coupled to the heart 10 by means of electrodes 29 and 28 on lead 14, as well as an atrial pulse generator circuit coupled to the heart 10 by means of atrial electrodes 20 and 21, located on lead 16. Similarly, pacing circuit 30 includes atrial and ventricular sense amplifiers in sense amplifier circuit 61, coupled to the atrium and ventricle by means of leads 14 and 16 as well. The ventricular sense amplifier provides for separate detection and identification of QRS-wave and T-wave signals, in a known manner. Control of timing and other functions within the pacemaker circuit is provided by digital controller/timer circuit 31, which includes a set of timers and associated logic. Digital controller/timer circuit 31 defines the basic pacing interval of the device, which may take the form of an A—A escape interval initiated on atrial sensing or pacing and triggering atrial pacing at the expiration thereof, or may take the form of a V—V escape interval, initiated on ventricular sensing or pacing and triggering ventricular pulse pacing at the expiration thereof. Digital controller/timer circuit 31 similarly defines the A-V escape interval, for use in a dual chamber embodiment. The specific values of the intervals defined are controlled by the microcomputer circuit by means of data and control bus 35.

Sensed atrial depolarizations are communicated to the digital controller/timer circuit 31 on the A-event line; ventricular depolarizations (QRS-waves) are communicated to the digital controller/timer circuit 31 on the V event line; and ventricular repolarizations (T-waves) are connected to circuit 31 on the T-wave line. In order to trigger generation of a ventricular pacing pulse, digital controller/timer circuit 31 generates a trigger signal on the V trig line; similarly, in order to trigger an atrial pacing pulse, digital controller/timer circuit 31 generates a trigger pulse on the A trig line. It is to be understood that while a dual chamber pacemaker is illustrated, the antenna is equally useful in single chamber pacemakers, and other types of implantable devices that are part of a telemetric system.

In the embodiment illustrated in FIG. 1, the pacemaker is provided with a piezo electric sensor 45 which is intended to monitor patient activity, in order to allow provision of rate responsive pacing, such that the defined pacing rate (A—A escape interval or V—V escape interval) increases with increased demand for oxygenated blood. Sensor 45 generates electrical signals in response to sensed physical activity which are processed by activity circuit 58 and provided to digital controller/timer circuit 31. Activity circuit 58 and associated sensor 45 may correspond to the circuitry disclosed in U.S. Pat. No. 5,052,388, issued to Betzold et al., and U.S. Pat. No. 4,428,378, issued to Anderson et al. Alternately, QT time may be used as a rate indicating parameter, in which case no extra sensor is required.

Transmission to and from an external programmer 40 is accomplished by means of antenna 41 and associated RF transmitter and receiver 56, which serves both to demodulate received downlink telemetry and to transmit uplink telemetry. A crystal oscillator circuit (not shown) provides the basic timing clock for the circuit, while battery 32 provides power. Other circuitry, known in the pacemaker art, is illustrated at 62.

Microcomputer circuit 34 controls the operational functions of digital controller/timer 31, specifying which timing intervals are employed, and controlling the duration of the various timing intervals, via data and control bus 35. Microcomputer circuit 34 contains a microprocessor 50 and associated system clock 51 and RAM and ROM circuits 52 and 53, respectively. In addition, microcomputer circuit 34 may include a separate RAM/ROM chip 55. Microprocessor 50 is interrupt driven, operating in a reduced power consumption mode normally, and awakened in response to defined interrupt events, which may include delivery of atrial and ventricular pacing pulses as well as sensed atrial and ventricular depolarizations.

Figure 2:
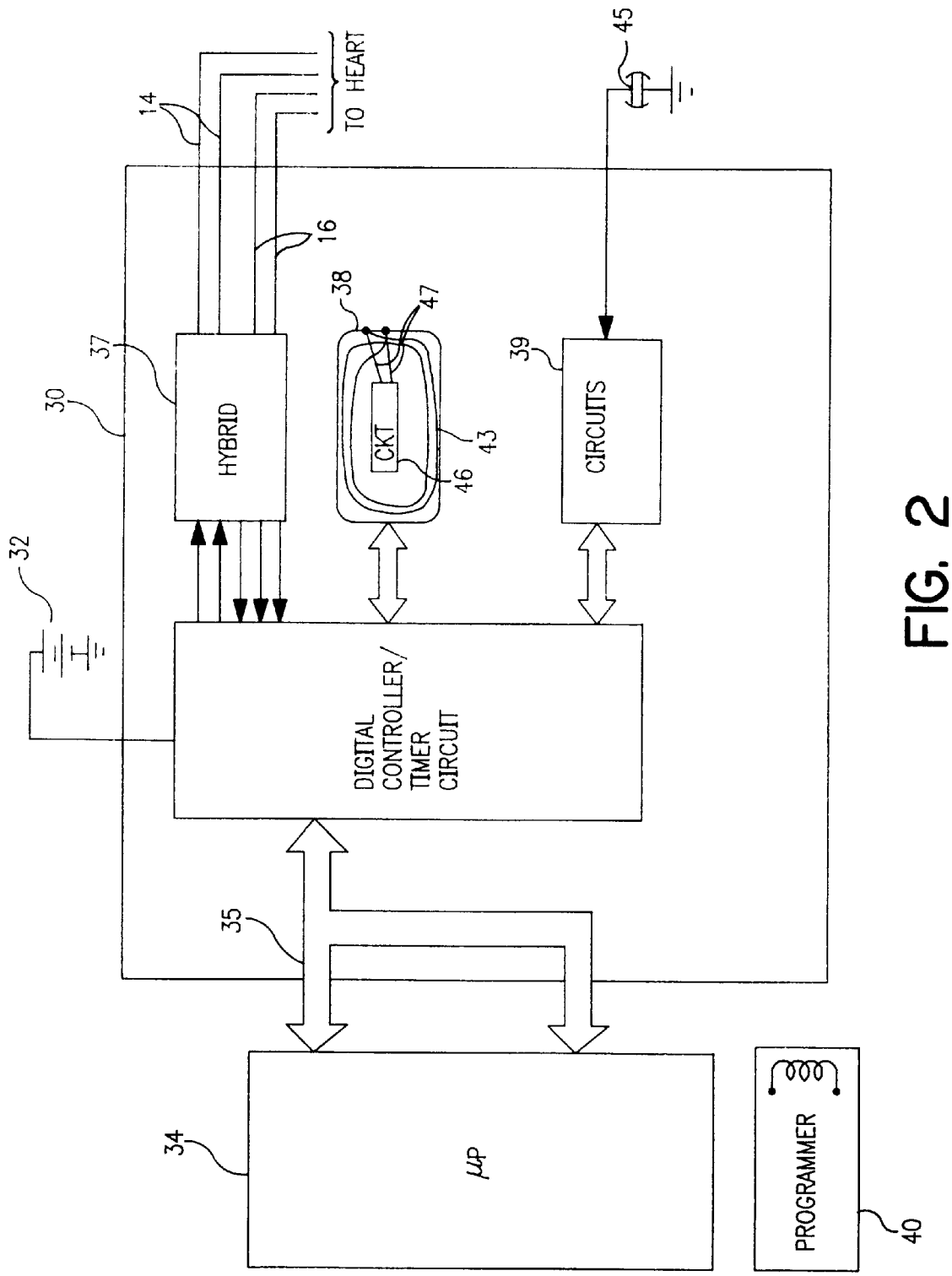
FIG. 2 is a block diagram illustrating the use of substrates carrying hybrid circuits in an implanted pacemaker, including a hybrid substrate fabricated with an air core antenna in accordance with this invention.

Referring now to FIG. 2, there shown is a block diagram of the same pacemaker as illustrated in FIG. 1, but modified to indicate the use of hybrid circuits in the implanted device. As is well known, the electronic design of an implantable device such as a cardiac pacemaker may utilize different architectures, and different degrees of digital and analog circuitry. In general, most commercial pacemakers today utilize a microprocessor and associated memory, as well as other hardware circuits which in turn can be classified as digital or analog. In production of the actual implantable pulse generator device, or pacemaker, different circuit platforms are utilized. Some of these circuits are mounted on "hybrids" or substrates which carry interconnected circuit portions. FIG. 2 illustrates, solely by way of example, a pacemaker showing two different hybrids, 37 and 38, which carry some of the circuits as discussed in connection with FIG. 1. For example, hybrid 37 contains the amplifier output circuit and the sense amplifiers. Another hybrid is shown at 38, which may carry other circuitry 46; and is illustrated having wound thereon, in accordance with this invention, an air core antenna 43, connected by wiring 47 to the circuitry 46. The air core antenna 43 communicates with programmer 40, and is interconnected through circuitry 46 to digital controller timer circuit 31. Block 39 is shown as including other circuits, as are required in a modern pacemaker. It is to be understood that the purpose of FIG. 2 is simply to illustrate the use of hybrids in the production of an implantable medical device, and is not intended to specify any particular arrangement of circuits or architecture for carrying out the functional operations of the implanted device.

Figure 3A:
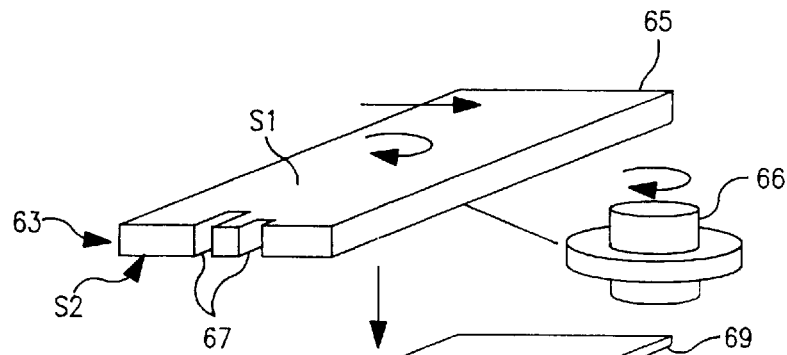
FIG. 3a–3f is a series of perspective diagrams illustrating the production process for making the air core antenna of this invention.

Referring now to FIGS. 3a–3f, there is shown a sequence of illustrations of the process of fabricating the air core antenna on a substrate 65. As illustrated in FIG. 3a, a substrate 65 is provided that initially has rough edges, and is to be milled to the exact dimensions for incorporation into the implantable pacemaker or other medical device. The substrate has opposing substantially planar surfaces S1, S2. The outer boundaries of the substrate provide a perimeter with an edge 63, having a predetermined thickness. The substrate also is provided with connection pads 67, shown as being within notches in the substrate. The process of milling the hybrid element to dimensions and positioning the coil around it is undertaken before any other components are mounted on the substrate; the substrate with coil will then be subsequently handled as one component during the further fabrication of the device.

Figure 3B:

A substrate 65 is placed on top of a rotatable support, not illustrated in FIGS. 3a–3f, which support suitably has position reference pins to fit into reference holes in the substrate, as well as a clamp or vacuum for fixing the substrate to the support. A specially shaped grinding element or fraise 66 is used to mill the edges 63 to the exact dimensions, and to mill the groove 65 at the same time; alternately, the edges and groove can be milled separately. The milling step thus transforms the substrate from the condition shown in FIG. 3a to the condition as illustrated in FIG. 3b, where the groove has been milled. The substrate is rotated and the required outer dimensional profile or perimeter of the substrate is created by controlling the radial distance of the fraise 66 to the support. This can be accomplished by a conventional servo mechanism, a stepper motor, reference profile disk, etc. Thus, the combined milling step produces the substrate altered as shown in FIG. 3b, having a groove 68 around the entire outer perimeter, of a dimension for receiving the coil antenna.

Figure 3C:
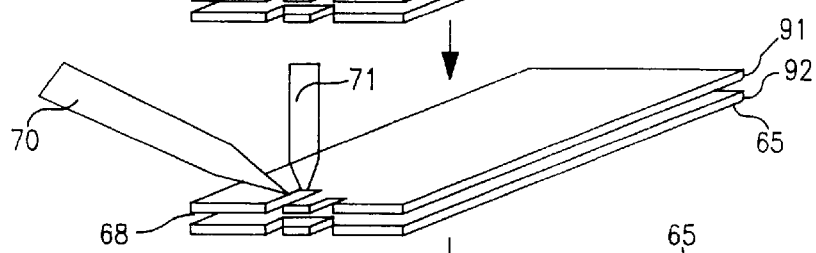
Figure 3D:
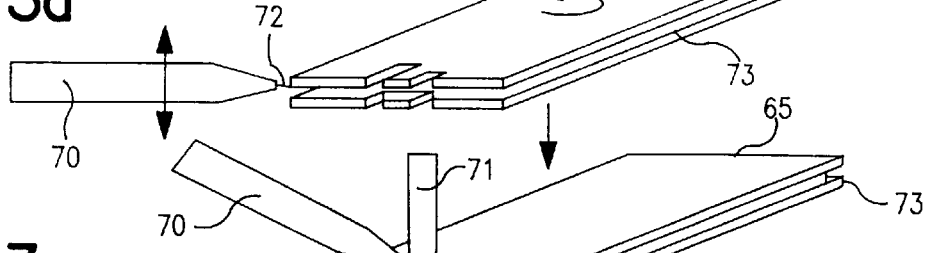
Figure 3E:
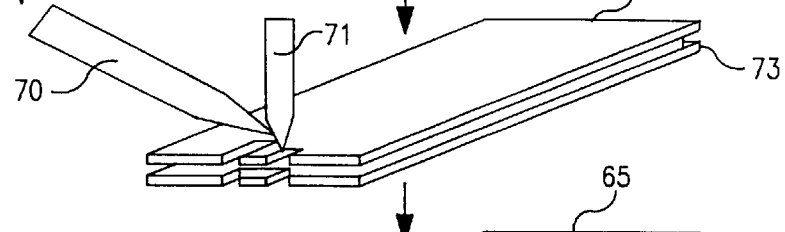
Figure 3F:
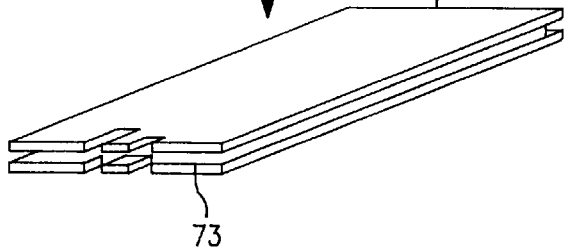

Next, as illustrated at FIGS. 3c and 3d, the coil is wound in the groove, using a position-controllable wire guide 70. The wire guide first positions one end of the wire at a first of the connection pads 67, and a welding or soldering element 71 fixes the wire end to a first of the connection pads. The wire 72 is guided by guide 70 while the substrate is rotated a given number of times corresponding to the coil windings, or loops until the coil 73 is fully positioned within groove 68. When this has been done, the wire is guided to the other connection pad 67, where it is fixed in position by element 71, as illustrated in FIG. 3e, after which the wire is cut and trimmed. At this point, the antenna product, illustrated in FIG. 3f, has a completed coil 73 within the grooves, and the two ends of the coil are available at connection pads 67 for connection to other circuits to be positioned on the substrate.

Figure 4:
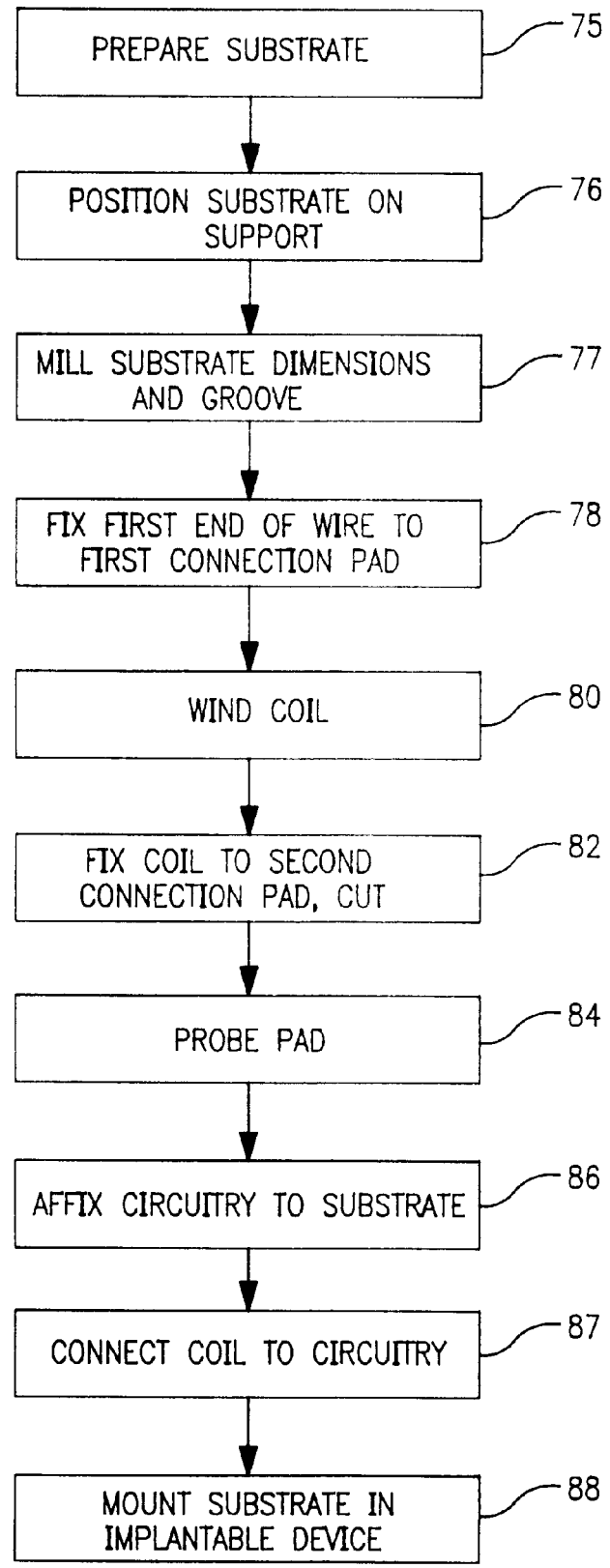
FIG. 4 is a flow diagram illustrating the primary steps in the method of making an air core antenna for use in an implantable device, in accordance with this invention.

Referring to FIG. 4, there is shown a flow diagram illustrating the primary steps in the method of producing the air coil antenna in accordance with this invention. As illustrated at 75, the substrate is first prepared for fabrication, which includes cutting the substrate and providing pads 67, which enable electrical connection of the air coil antenna to other circuitry. At 76, the substrate is positioned on a rotatable support preparatory to the milling operation. The milling operation at 77 comprises rotating the substrate on the support and grinding the substrate so as to produce the groove 68, and properly dimensioning the remaining upper and lower edges 91, 92 of original edge 63 (FIG. 3c). An important part of this step is to mill the groove to the planned width and depth in order to accommodate the antenna. Following this, as illustrated at 78, a first end of the wire is provided and fixed to a first one of connection pads 67, by soldering or an equivalent step. After this, the coil is wound, at 80 preferably under servo control by rotating substrate 65 with respect to the wire guide element 70, so that the wire is drawn out of element 70 and tightly wound within the grove. After this at 82, when the specified number of windings have been accomplished, the coil is fixed to the second connection pad, and cut, thereby completing physical placement of the coil antenna into the groove of the hybrid. Following this, as illustrated at 84, the two connection pads are probed. The probing operation suitably involves applying a current pulse through the coil. This results in heating of the coil which causes all of the windings to be baked together such that the insulation around the windings melts to just a degree as to fuse the windings together while maintaining electrical isolation between the windings. Further, it is desirable at this step to test the coil to determine that the coil inductance and resistance are within desired specifications. Following this, as illustrated at steps 86, 87, 88, the circuitry is affixed to the substrate; the coil is connected to the circuitry; and the substrate is mounted in the device.

As used in this invention, a typical hybrid element 65 has a finished planar surface area of about 3 to 6 $cm^2$; the coil windings, fixed within the groove, have a loop area of just less than the surface area. A typical substrate thickness is in the range of 0.8 to 1.5 mm; the groove has a thickness of about 0.5 to 0.7 mm, and a depth of about 0.8 to 1.5 mm. The wire used in the antenna is suitably 44 AWG or 46 AWG copper wire with single build polyamide insulation and a single build epoxy bond coat.

I claim:

1. An implantable medical device, having means for being in telemetric communication with an external device, comprising:

a substrate, said substrate having a thickness and an outer perimeter;

said substrate having a groove within said thickness around said perimeter;

an antenna coil wound within said groove; and a circuit mounted on said substrate and electrically connected to said antenna coil.

2. The device as described in claim 1, wherein said medical device is an implantable pacemaker, and said circuit further comprises means for receiving signals picked up by said coil from said external device, and means for connecting signals to said coil antenna for transmission to said external device.

3. The device as described in claim 1, wherein said substrate has a thickness in the range of 0.8 to 1.5 mm, and said groove has a thickness of about 0.5 to 0.7mm.

4. The device as described in claim 3, wherein said groove has a depth in a range of 0.8 to 1.5 mm.

5. The device as described in claim 1, wherein said antenna coil comprises copper wire.

6. The device as described in claim 1, wherein said groove has a perimeter defining an area of about 3 to 6 $cm^2$.

7. An implantable pacemaker, said pacemaker having generator means for generating pacing pulses, telemetric means for receiving telemetric programming signals from an external source, and control means for controlling pacemaker function in accordance with said received signals, said telemetric means comprising a substrate having first and second substantially planar surfaces with a thickness therebetween and a predetermined perimeter around said surfaces, a groove within said thickness and around said perimeter, and an antenna coil wound within said groove.

8. The pacemaker as described in claim 7, wherein said telemetric means comprises receiving circuitry mounted on one of said substrate surfaces, and connecting means for connecting said antenna coil electrically to said receiving circuitry.

9. The pacemaker as described in claim 8, comprising a plurality of hybrid circuits and a microprocessor circuit, and interconnecting means for interconnecting said telemetric means with at least one of said microprocessor and hybrid circuits.

10. A method of making an air core antenna for use in an implantable device, comprising:

providing a substrate having opposed substantially planar surfaces of a predetermined area and outer perimeter, said substrate having a predetermined thickness between said surfaces;

cutting a shallow groove within said thickness and around said perimeter;

positioning an antenna coil of a predetermined number of windings within said groove, so that said windings have a loop area just less than said predetermined area;

and providing connecting means for enabling an electrical connection to said antenna coil.

11. The method as described in claim 10, comprising rotating said substrate and cutting said substrate to said outer perimeter and cutting said groove during said rotating.

12. The method as described in claim 11, wherein said positioning step comprises rotating said substrate and winding said coil within said groove as said substrate is rotated.

13. The method as described in claim 12, comprising providing placing connection pads on said substrate, and connecting said coil to said connection pads.

14. The method as described in claim 13, comprising probing said antenna coil after said positioning and connecting.

15. The method as described in claim 14, wherein said positioning step comprises positioning a coil having a wire with insulation around it, and said probing comprises driving a current through said antenna coil, thereby fusing adjacent windings of said antenna coil.

16. The method as described in claim 14, wherein said probing comprises testing said antenna for predetermined electrical characteristics.

17. The method as described in claim 13, comprising placing an electrical circuit pattern on said substrate after positioning said antenna, connecting said antenna to said connection pads, and then connecting said circuit pattern to said connection pads.

18. A hybrid electrical unit, comprising:

a substrate having a predetermined thickness and an outer of perimeter;

a groove around said perimeter and within said thickness;

a coil with plural windings, positioned within said groove;

an electrical circuit fixed to said substrate; and connecting means for connecting said coil to said circuit, whereby said coil acts as an antenna.

\* \* \* \* \*